United States Patent
Mirisharif

(10) Patent No.: US 10,114,139 B1
(45) Date of Patent: Oct. 30, 2018

(54) MULTI-CAPACITOR LIQUID DETECTION DEVICE AND METHOD(S) OF USE

(71) Applicant: Z~Communications, Inc., Boulder, CO (US)

(72) Inventor: Seyedmohammad Mirisharif, Longmont, CO (US)

(*) Notice: Subject to any disclaimer, the term of this patent is extended or adjusted under 35 U.S.C. 154(b) by 0 days.

(21) Appl. No.: 15/583,431

(22) Filed: May 1, 2017

(51) Int. Cl.
- *G01N 27/22* (2006.01)
- *G01V 3/08* (2006.01)
- G01N 33/28 (2006.01)
- G01F 23/26 (2006.01)

(52) U.S. Cl.
CPC .............. *G01V 3/08* (2013.01); *G01F 23/263* (2013.01); *G01N 27/22* (2013.01); *G01N 33/2888* (2013.01)

(58) Field of Classification Search
CPC ..... G01V 3/08; G01F 23/263; G01N 33/2888
See application file for complete search history.

(56) References Cited

U.S. PATENT DOCUMENTS

| | | | |
|---|---|---|---|
| 4,315,822 A | 2/1982 | Jaisinghani | |
| 4,417,473 A * | 11/1983 | Tward | G01F 23/263 361/284 |
| 4,674,879 A | 6/1987 | Gregorig et al. | |
| 5,122,280 A | 6/1992 | Russell et al. | |
| 6,203,281 B1 | 3/2001 | Gurega | |
| 6,443,006 B1 | 9/2002 | Degrave | |
| 8,340,928 B2 | 12/2012 | Sun | |
| 2002/0116999 A1* | 8/2002 | Heger | G01F 23/265 73/304 C |
| 2012/0126026 A1* | 5/2012 | Sparks | A01G 25/167 239/64 |

* cited by examiner

*Primary Examiner* — Jermele M Hollington
*Assistant Examiner* — Alvaro Fortich
(74) *Attorney, Agent, or Firm* — Leyendecker & Lemire, LLC

(57) ABSTRACT

A multi-capacitor liquid detection device and method(s) of use is described. Embodiments of the multi-capacitor liquid detection device can include at least two capacitors being separated by a predetermined height. The multi-capacitor liquid detection device can be implemented to detect and differentiate between different types of immiscible liquids by measuring and comparing a dielectric constant between two or more capacitors. The multi-capacitor liquid detection device can be implemented to determine if a false detection of a liquid has been made by one of the capacitors.

20 Claims, 5 Drawing Sheets

MULTI-CAPACITOR LIQUID DETECTION DEVICE AND METHOD(S) OF USE

BACKGROUND

Electronic oil sensing methods currently include microwave line matching, microwave radar, ultraviolet intensity processing, density measurement, conductance measurement, magnetic sensor, and capacitive sensors. Each of the currently available methods has one or more drawbacks for use in low cost applications.

Microwave line matching requires (i) accurate calibration including calibration for temperature, (ii) a probe to be periodically cleaned, (iii) accurate installation and onsite calibration, and (iv) components that are very costly. Microwave radar requires accurate calibration and excessive data processing in addition to high costs due to components and expertise required to build the microwave radar. Ultraviolet intensity processing requires regular cleaning, accurate calibration, and image processing. Further, ultraviolet intensity processing is installation dependent and requires high costs dues to components and the expertise required to build a system. Density measurement systems typically include changing an existing system for installation, are direction dependent, and have high costs associated with implementing the systems. Conductance measurement systems have very limited options for use with various liquids, are typically used for oil degradation or liquid level determination, and often produce false positives. Magnetic sensors are limited in the types of liquids available to be used with and are usually implemented to determine liquid levels. Capacitive sensors have low resolution, are typically implemented for determining liquid levels, and require changes to an existing system for installation.

Low cost sensors currently available have several drawbacks including, but not limited to, temperature sensitivity, liquid purity sensitivity, liquid flow sensitivity, residue build up, and low measurement resolution.

DETAILED DESCRIPTION

Figure 1:
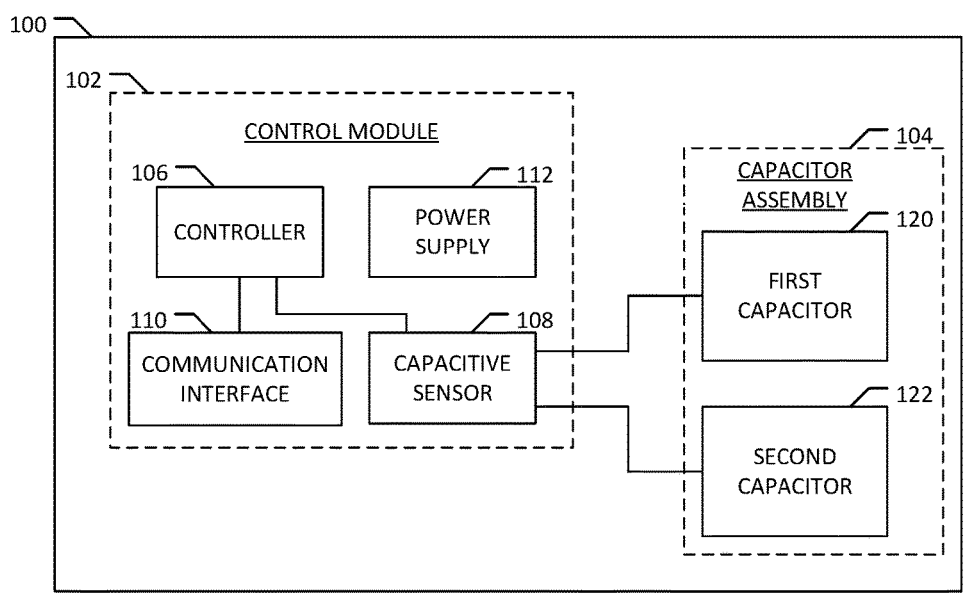
FIG. 1 is a block diagram of a multi-capacitor liquid detection device according to one embodiment of the present invention.

Embodiments of the present invention include a multi-capacitor liquid detection device and method(s) of use. The multi-capacitor liquid detection device can be implemented to detect and differentiate between different types of immiscible liquids by measuring and comparing a dielectric constant between two or more capacitors. In one embodiment, a first capacitor and a second capacitor having different heights (or widths) can be implemented. The multi-capacitor liquid detection device can be implemented to determine if a false detection of a liquid has been made by one of the capacitors. In one instance, the multi-capacitor liquid detection device can verify a detection of a liquid by one of the capacitors. Embodiments of the present invention can be implemented to differentiate between two immiscible liquids in an environment by measuring a relative permittivity of one capacitor for detection of a liquid and measuring a second relative permittivity of another capacitor to prevent false reports of a detection of a liquid.

In one embodiment, the multi-capacitor liquid detection device can include, but is not limited to, a controller, a capacitive sensor, a first capacitor, a second capacitor, a mounting plate, and a power source. The first capacitor and the second capacitor can each include a pair of conductive plates. In a typical implementation, the conductive plates can be defined by a length, a width, and a thickness. The plates are generally oriented vertical with the width defining a height of each of the plates. The first and second capacitor can each be coupled to the mounting plate, with the mounting plate located on top of the capacitors. The first pair of conductive plates can have a first height and the second pair of conductive plates can have a second height. Typically, a height differentiation between the first pair and the second pair of conductive plates can be predetermined. The height differentiation between the plates of the capacitors can be calculated to help to detect a presence of liquid while negating false reports. In one instance, the first capacitor can be implemented to detect a presence of liquid and the second capacitor can be implemented to verify a liquid detected by the first capacitor.

In one embodiment, the controller, the capacitive sensor, the first capacitor, the second capacitor, the mounting plate and the power source can be configured as a device. The device can be implemented to detect liquid presence by determining a dielectric constant (or relative permittivity) of the first capacitor and the second capacitor. The device can provide a false free report of liquid detection by using a combination of the two pairs of capacitor plates having calculated differing heights in a dual liquid container where the liquids are immiscible.

Typically, the device can be configured such that a gap between each of the capacitor plates can be based on a liquid being detected to prevent a need for cleaning of the device after each test. Embodiments of the present invention can implement the idea of capacitance difference instead of absolute capacitance value to prevent a need of calibration for different environments. In some embodiments, the device can be configured to be combined with a resistive sensor to increase detection options. Generally, the device can implement a surface line capacitor combined with base capacitor plates for high resolution measurements.

In one example, two capacitors can be arranged in a relative location to each other to detect and differentiate between different types of immiscible liquids by measuring a dielectric constant (or relative permittivity) of the two capacitors. Each of the capacitors can include a pair of electrically conductive plates. The device can use a combination of measured capacitance to report a presence and type of liquid in a dual liquid container. Typically, a condition for the two liquids can include substantially different dielectric constants and be immiscible with one another. As one example, immiscible liquids that the device can be implemented with are oil and water. Of note, oil and water are provided for illustrative purposes only and are not meant to be limiting.

As previously mentioned, the device can include two pairs of conductive plates implemented as the first capacitor and the second capacitor. The first capacitor (hereinafter C1) can be considered as a detection capacitor and the second capacitor (hereinafter C2) can be a false prevention capacitor or verification capacitor. C1 can have a greater height than C2. The combination of C1 and C2 together can provide a false free report of immiscible liquids measured between the conductive plates of the capacitors. As previously mentioned, when testing, the liquids should be immiscible and have different dielectric constants.

To do a calculation of the basis behind the multi-capacitor liquid detection device, the two liquids can be referred to as E1 and E2. E1 and E2 represent the two liquids where the dielectric constant of E1 is not equal to E2 which means one of the liquids has a higher dielectric constant. In this example, E1 has a larger dielectric constant than E2. If a dielectric measured by C1 is air that would indicate air is located between both pairs of conductive plates which results in no liquid being detected by the device. If the measurement by C1 shows the higher dielectric constant of E1, this may indicate the device may be dipped in the higher dielectric constant E1 which would result in detection of E1. However, if the measurement by C1 shows the dielectric constant of E2, the device cannot jump to a conclusion for detection of E2 and this could be a false report which is a possible result when using a single capacitor sensor. The reason can be explained by the result where measuring the lower dielectric of E2 is not clear that C1 is dipped in E2 or a part of C1 is dipped in E1 (higher dielectric) and the rest is empty (e.g., air). Stated alternatively, the detection of E2 could be either the detection of E2 or a combination of E1 and air based on the dielectric measured.

To illustrate a false report and the problem that a single capacitor cannot generate a reliable result in a subject environment with two immiscible liquids, there are three possible scenarios. First, a dielectric measurement by the capacitor may be "1," which can indicate no liquid between the conductive plates and a dielectric measurement equal to the dielectric constant of air. This result can be trusted since the dielectric constant of air will be the lowest value in the subject environment. Second, a dielectric measurement by the capacitor may indicate a higher dielectric measurement approximately equal with a dielectric constant of the liquid with the highest dielectric constant. This result can be trusted since there would be no liquid in the subject environment that has a higher dielectric constant. Third, a dielectric measurement by the capacitor may indicate a lower dielectric measurement approximately equal with a dielectric constant of the liquid with the lowest dielectric constant. There are two possible conditions for this result. The liquid between the conductive plates of the capacitor may be the second liquid. Alternatively, there may be a layer of the first liquid between the conductive plates and the rest may be air indicating that a combined capacitance of the air and the first liquid is equal to a capacitance measured when the plates are filled with the second liquid between them.

The following equations show a condition where the third scenario can happen.

$$C = \varepsilon_0 \varepsilon_r \frac{A}{d} \qquad \text{Equation 1}$$

Referring to equation 1, C is a capacitance between plates measured in farads (F), $\varepsilon_0$ is the dielectric constant of the space $8.85 \times 10^{-12}$ measured in farads per meter (F/m), $\varepsilon_r$ is the dielectric constant of a material between the plates, A is the area of each plate equal to L×H measured in meters squared (m²) and d is a distance between plates measured in meters (m).

According to equation 2, a capacitance measured between two plates when the plates are dipped in the second liquid is:

$$C_{E2} = \varepsilon_0 E_2 \frac{L \times H}{d} \qquad \text{Equation 2}$$

According to equation 3, the capacitance between two plates when a part of the plates is in the first liquid and the rest is in air is shown in equation 3.

$$C_{E1} = \varepsilon_0 E_1 \frac{L \times \Delta H}{d} + \varepsilon_0 \frac{L \times (H - \Delta H)}{d} \qquad \text{Equation 3}$$

The error happens when $C_{E1}=C_{E2}$, which is in long form in equation 4.

$$\varepsilon_0 E_2 \frac{L \times H}{d} = \varepsilon_0 E_1 \frac{L \times \Delta H}{d} + \varepsilon_0 \frac{L \times (H - \Delta H)}{d} \qquad \text{Equation 4}$$

Simplifying equation 4 will result in equation 5.

$$E_2 H = E_1 \Delta H + H - \Delta H \qquad \text{Equation 5}$$

A thickness of a layer of the first liquid at the time of error can be determined by equation 6.

$$\Delta H = \frac{E2 - 1}{E1 - 1} H \qquad \text{Equation 6}$$

Now that the condition of the error has been explained, a solution would be to add a second pair of plates high enough, for instance at least at a distance of ΔH, to detect air on top of a layer of the first liquid and use the combination of two capacitors to make a determination of liquid detection.

The multi-capacitor liquid detection device can be implemented to overcome the deficiencies of a single capacitor device for detecting liquids. For instance, as previously described, a single capacitor device can allow a condition where a false report is generated. The multi-capacitor liquid detection device can limit or remove false reports by implementing a second pair of conductive plates to detect air on top of the layer of the first liquid and use the combination of two capacitors to make a determination of liquid detection.

As shown in the first equation, a dimension of the conductive plates can determine a value of the capacitor. To prevent cleaning after each measurement, a distance between the plates for each capacitor should be substantially larger than a drop size of the liquids being tested in the two liquid container. As can be appreciated, the drop size of the container depends on a surface tension of the liquids and a tension between the liquids and the coating of the plates. In one embodiment, the distance between the plates can be equal or greater than two times the liquid drop diameter. By implementing this constraint, a dielectric measurement can be independent from residue and cleaning because a majority of the volume between the plates is for the liquid under test and not any residue.

Embodiments of the present invention can further include a calibration free capacitance sensor. Generally, the dielectric constant of air can be implemented as a reference and device can measure a difference between a detected capacitance of the liquids and the reference to make a determination liquid detection. As can be appreciated, an absolute value of capacitance is not important. By not relying on absolute capacitance, any reason (e.g., temperature change) the absolute capacitance changes, the difference between the liquids and air will stay the same. Of note, by using a difference in detected capacitance, the device does not need to be calibrated in different environments.

The multi-capacitor liquid detection device can be implemented to detect and differentiate between two immiscible liquids. However, if one of the liquids has electrical conductivity, the device can be combined with a resistive sensor to increase a detection range to more than two liquids. As mentioned previously, one of the biggest advantages of this device is that the device does not need to be cleaned after each measurement.

A resolution of a measurement can depend on a dielectric constant of a liquid and an available technology for capacitance measurement. In one embodiment, to increase measurement resolution, a height of the capacitor plates can be reduced in addition to reducing a distance between each pair of plates to be able to measure a similar capacitance. These modifications can be implemented with the combination of capacitors to increase a precision of measurement made by the multi-capacitor liquid detection device.

In one embodiment, the multi-capacitor liquid detection device can be a self-contained assembly that can be adapted to float on a body water. In one example, the device can be implemented to detect when oil or other liquids harmful to an eco-system are located in a body of water. In another example, the device can be mounted inside a container at a predetermined height to determine when a non-desirable liquid is present or when an unacceptable level of a non-desirable liquid has been reached. In yet another example, the device can be operatively implemented in a pump control circuit to provide an automatic shut-off of the pump when a non-desirable liquid has been detected. Of note, the multi-capacitor liquid detection device implements a verification means for ensuring a pump, or other devices are not shut-off based on a false detection of the non-desirable liquid.

The present invention can be embodied as devices, systems, methods, and/or computer program products. Accordingly, the present invention can be embodied in hardware and/or in software (including firmware, resident software, micro-code, etc.). Furthermore, the present invention can take the form of a computer program product on a computer-usable or computer-readable storage medium having computer-usable or computer-readable program code embodied in the medium for use by or in connection with an instruction execution system. In one embodiment, the present invention can be embodied as non-transitory computer-readable media. In the context of this document, a computer-usable or computer-readable medium can include, but is not limited to, any medium that can contain, store, communicate, propagate, or transport the program for use by or in connection with the instruction execution system, apparatus, or device.

The computer-usable or computer-readable medium can be, but is not limited to, an electronic, magnetic, optical, electromagnetic, infrared, or semiconductor system, apparatus, device, or propagation medium.

Terminology

The terms and phrases as indicated in quotation marks (" ") in this section are intended to have the meaning ascribed to them in this Terminology section applied to them throughout this document, including in the claims, unless clearly indicated otherwise in context. Further, as applicable, the stated definitions are to apply, regardless of the word or phrase's case, to the singular and plural variations of the defined word or phrase.

The term "or" as used in this specification and the appended claims is not meant to be exclusive; rather the term is inclusive, meaning either or both.

References in the specification to "one embodiment", "an embodiment", "another embodiment," "a preferred embodiment", "an alternative embodiment", "one variation", "a variation" and similar phrases mean that a particular feature, structure, or characteristic described in connection with the embodiment or variation, is included in at least an embodiment or variation of the invention. The phrase "in one embodiment", "in one variation" or similar phrases, as used in various places in the specification, are not necessarily meant to refer to the same embodiment or the same variation.

The term "couple" or "coupled" as used in this specification and appended claims refers to an indirect or direct physical connection between the identified elements, components, or objects. Often the manner of the coupling will be related specifically to the manner in which the two coupled elements interact.

The term "directly coupled" or "coupled directly," as used in this specification and appended claims, refers to a physical connection between identified elements, components, or objects, in which no other element, component, or object resides between those identified as being directly coupled.

The term "approximately," as used in this specification and appended claims, refers to plus or minus 10% of the value given.

The term "about," as used in this specification and appended claims, refers to plus or minus 20% of the value given.

The terms "generally" and "substantially," as used in this specification and appended claims, mean mostly, or for the most part.

Directional and/or relationary terms such as, but not limited to, left, right, nadir, apex, top, bottom, vertical, horizontal, back, front and lateral are relative to each other and are dependent on the specific orientation of a applicable element or article, and are used accordingly to aid in the description of the various embodiments and are not necessarily intended to be construed as limiting.

The term "software," as used in this specification and the appended claims, refers to programs, procedures, rules, instructions, and any associated documentation pertaining to the operation of a system.

The term "firmware," as used in this specification and the appended claims, refers to computer programs, procedures, rules, instructions, and any associated documentation contained permanently in a hardware device and can also be flashware.

The term "hardware," as used in this specification and the appended claims, refers to the physical, electrical, and mechanical parts of a system.

The terms "computer-usable medium" or "computer-readable medium," as used in this specification and the appended claims, refers to any medium that can contain, store, communicate, propagate, or transport the program for use by or in connection with the instruction execution system, apparatus, or device. The computer-usable or computer-readable medium may be, for example but not limited to, an electronic, magnetic, optical, electromagnetic, infrared, or semiconductor system, apparatus, device, or propagation medium. By way of example, and not limitation, computer readable media may comprise computer storage media and communication media.

The term "signal," as used in this specification and the appended claims, refers to a signal that has one or more of its characteristics set or changed in such a manner as to encode information in the signal. It is to be appreciated that wireless means of sending signals can be implemented including, but not limited to, Bluetooth, Wi-Fi, acoustic, RF, infrared and other wireless means.

An Embodiment of a Multi-Capacitor Liquid Detection Device

Referring to FIG. 1, a block diagram of an embodiment 100 showing a multi-capacitor liquid detection device is illustrated. The multi-capacitor liquid detection device 100 can be implemented to detect one or more liquids and prevent false reports of a liquid being detected. Generally, the multi-capacitor liquid detection device 100 can be placed in an environment including a first liquid, a second liquid, and air. In one instance, the device 100 can be placed in an environment where oil and water may mix.

As shown, the multi-capacitor liquid detection device 100 can typically include a control module 102 and a capacitor assembly 104. The control module 102 can be connected to the capacitor assembly 104. In one embodiment, the control module 102 and the capacitor assembly 104 can be connected such that both the control module 102 and the capacitor assembly 104 are subjected to testing conditions. In another embodiment, the control module 102 may be remotely located from the capacitor assembly 104. As can be appreciated, the control module 102 can be operatively connected to the capacitor assembly 104 when remotely located from the capacitor assembly 104.

The control module 102, can include, but is not limited to, a controller 106, a capacitive sensor 108, a communication interface 110, and a power supply 112. Typically, the capacitor assembly 104 can include two or more capacitors. In one embodiment, the capacitor assembly 104 can include, but is not limited to, a first capacitor 120 and a second capacitor 122.

In one embodiment, the controller 106 can be a microcontroller. The microcontroller 106 can typically include, but is not limited to, one or more processor cores, memory, and one or more programmable input/output peripherals. The capacitive sensor 108 can be implemented to measure a capacitance of the first capacitor 120 and the second capacitor 122. The microcontroller 106 can determine a relative permittivity of the first capacitor 120 and/or the second capacitor 122 based on a measured capacitance by the capacitive sensor 108. Based on the relative permittivity, the microcontroller 106 can determine if the first liquid, the second liquid, or air has been detected by either of the capacitors 120, 122. For instance, the microcontroller 106 can compare the relative permittivity of either of the capacitors 120, 122 to a dielectric constant of the first liquid, the second liquid, and air.

The communication interface 110 may include wired and wireless communication protocols for sending data from the microcontroller 106 to a user device. In one embodiment, where the device 100 may be implemented as part of another system, the communication interface 110 may send a signal to a controller of the other system. For instance, the communication interface 110 may be communicatively connected to a controller of a pump. The microcontroller 106 may send a signal to shut the pump off via the communication interface 110 to the pump controller. The power supply 112 can be implemented to provide power to each of the components of the multi-capacitor liquid detection device 100.

Figure 2:
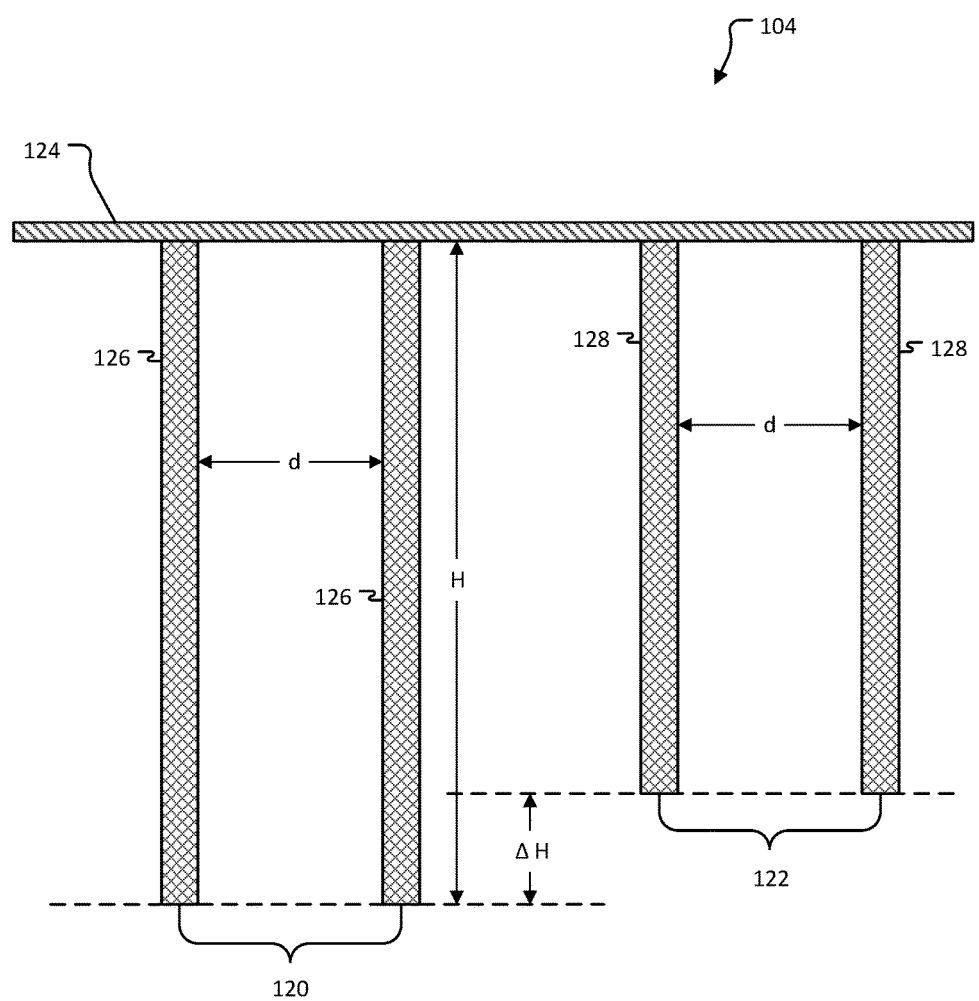
FIG. 2 is a cross-sectional view of a capacitor assembly according to one embodiment of the present invention.

Referring to FIG. 2, a cross-sectional view of the capacitor assembly 104 is illustrated. As shown, the capacitor assembly 104 can further include a mounting plate or chassis 124. The mounting plate 124 can be implemented to position the first capacitor 120 in a fixed relationship to the second capacitor 122. In some embodiments, components of the control module 102 and the capacitor assembly 104 may each be coupled to the mounting plate 124 to form a self-contained device.

The first capacitor 120 can include a first pair of plates 126 and the second capacitor 122 can include a second pair of plates 128. In one embodiment, the first capacitor 120 and the second capacitor 122 can each be parallel plate capacitors. Typically, the first pair of plates 126 and the second pair of plates 128 can be coupled to the mounting plate 124 with a top side of each of the plates 126, 128 coupled to a bottom side of the mounting plate 124. As shown, the first pair of plates 126 can have a greater height than the second pair of plates 128.

As previously mentioned, the height of the first pair of plates 126 and the height of the second pair of plates 128 can be determined based on the dielectric constant of air and two liquids being detected.

Referring back to equation 6, a difference in height between the first pair of plates 126 and the second pair of plates 128 (e.g., $\Delta H$) can be predetermined based on two immiscible liquids the device 100 will be implemented to detect. In one example, the device 100 can be implemented in an oil in water system where the device 100 can be implemented to detect oil. Based on the previously presented equation 6 in an example oil in water system, $\Delta H$ can be equal to, or greater than, $\frac{1}{13}$ a height of the taller capacitor. Stated alternatively, a difference in heights between the first capacitor 120 and the second capacitor 122 should be at least 0.0769 multiplied by a height of the first capacitor 120. For example, where a height of the first pair of plates 126 of the first capacitor 120 is 5 mm, a difference in height between the first pair of plates 126 and the second pair of plates 128 should be at least 0.38 mm. Of note, the difference in height between the first pair of plates 126 and the second pair of plates 128 can be greater than the minimum distance.

Figure 3:
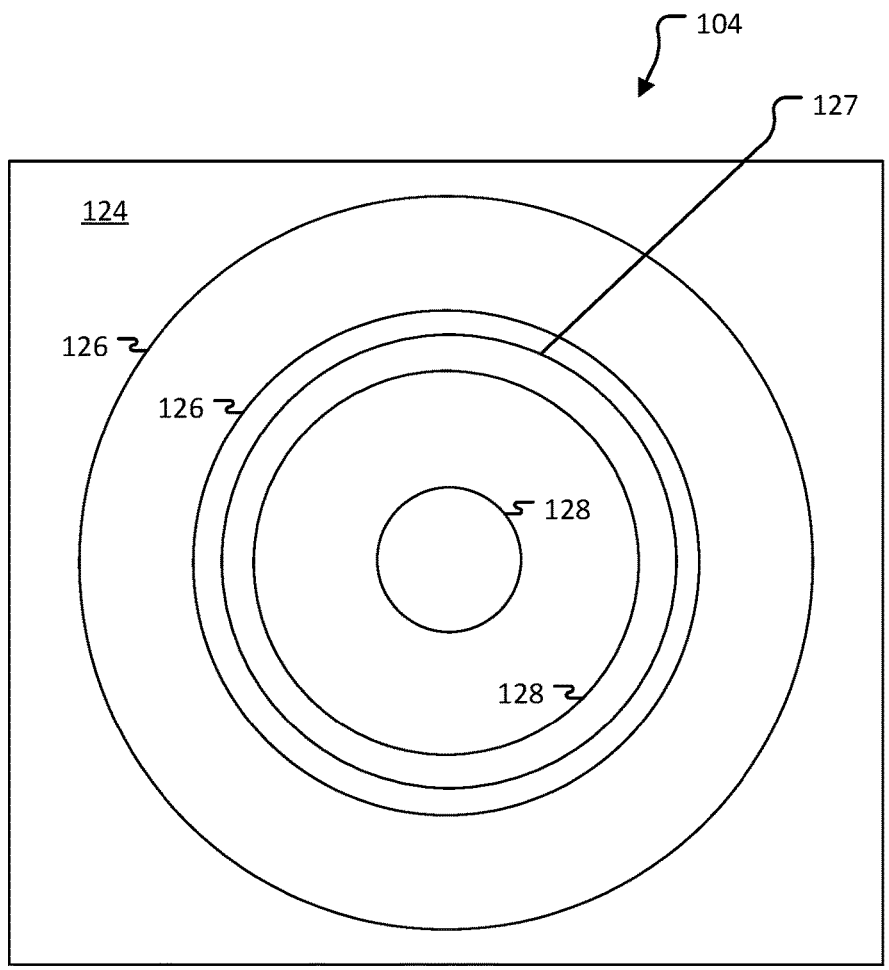
FIG. 3 is a bottom view of a capacitor assembly according to one embodiment of the present invention.

Referring to FIG. 3, a bottom view of one example configuration of the capacitor assembly 104 is illustrated. As shown, the mounting plate 128 can have a substantially rectangular shape and the first pair of plates 126 and the second pair of plates 128 can be positioned to have substantially circular shapes. FIG. 3 shows one proposed arrangement for the capacitor plates for illustrative purposes only. As can be appreciated, an actual arrangement of the capacitor plates can include, but is not limited to, side by side, concentric circles, rectangular, or any other shape as long as the height difference can be considered.

In some embodiments, the capacitor assembly 104 can further include a shield 127 located between the first pair of plates 126 and the second pair of plates 128. The shield 127 can be implemented to isolate the first capacitor 120 from the second capacitor 122. In one embodiment, the shield 127 can be a ground wire.

Described hereinafter is one example of a multi-capacitor liquid detection device. The example multi-capacitor liquid detection device is provided for illustrative purposes only and is not meant to be limiting. The multi-capacitor liquid detection device can include, but is not limited to, a control module operatively connected to a capacitor assembly. The control module and the capacitor assembly can both be coupled to a mounting plate, with the control module on one side of the mounting plate and the capacitor assembly located on the other side of the mounting plate. After the control module and the capacitor assembly have been coupled to the mounting plate and operatively connected to each other, the components can be coated with rubber to protect the device. The mounting plate can include one or more holes for allowing air to escape when the device is placed in a liquid.

The control module can include, but is not limited to, a microcontroller, a capacitive sensor connected to the microcontroller, a communication interface, and a power supply. The capacitive sensor can be a FDC2114 capacitive sensor manufactured by Texas Instruments. The communication interface can provide wireless communication to a user device. For instance, the communication interface may be Bluetooth or Wi-Fi. As can be appreciated, the power supply can be implemented to provide power to the components of the control module and the capacitor assembly.

The capacitor assembly can include, but is not limited to, a first capacitor including a first pair of parallel plates and a second capacitor including a second pair of parallel plates. The first pair of parallel plates and the second pair of parallel plates can be brass ribbons having different widths. For instance, a first brass ribbon having a first width can be implemented to make the first pair of parallel plates. A second brass ribbon having a second width can be implemented to make the second pair of parallel plates. The first brass ribbon can have a greater width than the second brass ribbon. Each of the brass ribbons can be coupled to the mounting plate vertically, with the width of the brass ribbon defining a height of each of the plates. Similar to the configuration illustrated in FIG. 3, the brass ribbons can be coupled to the mounting plate to form circular parallel plates with the first pair of plates located outside of the second pair of parallel plates. As can be appreciated, the device can be implemented with the capacitor assembly side facing down.

Of note, since the first capacitor has a greater area than the second capacitor, relative changes to the capacitance measured for each capacitor can be used instead of an actual capacitance at the time of measurement. For instance, each capacitor can be measured for a base capacitance, for instance with just air, and then the microcontroller can use a change in capacitance to determine when a liquid has been detected.

The mounting plate can include vias or apertures to operatively connect the first capacitor and the second capacitor to the capacitive sensor. For instance, coax cable or other conductive cable can be coupled to the first capacitor and the second capacitor and then connected to inputs of the capacitive sensor.

A Method to Verify a Detection of a Liquid

Figure 4:
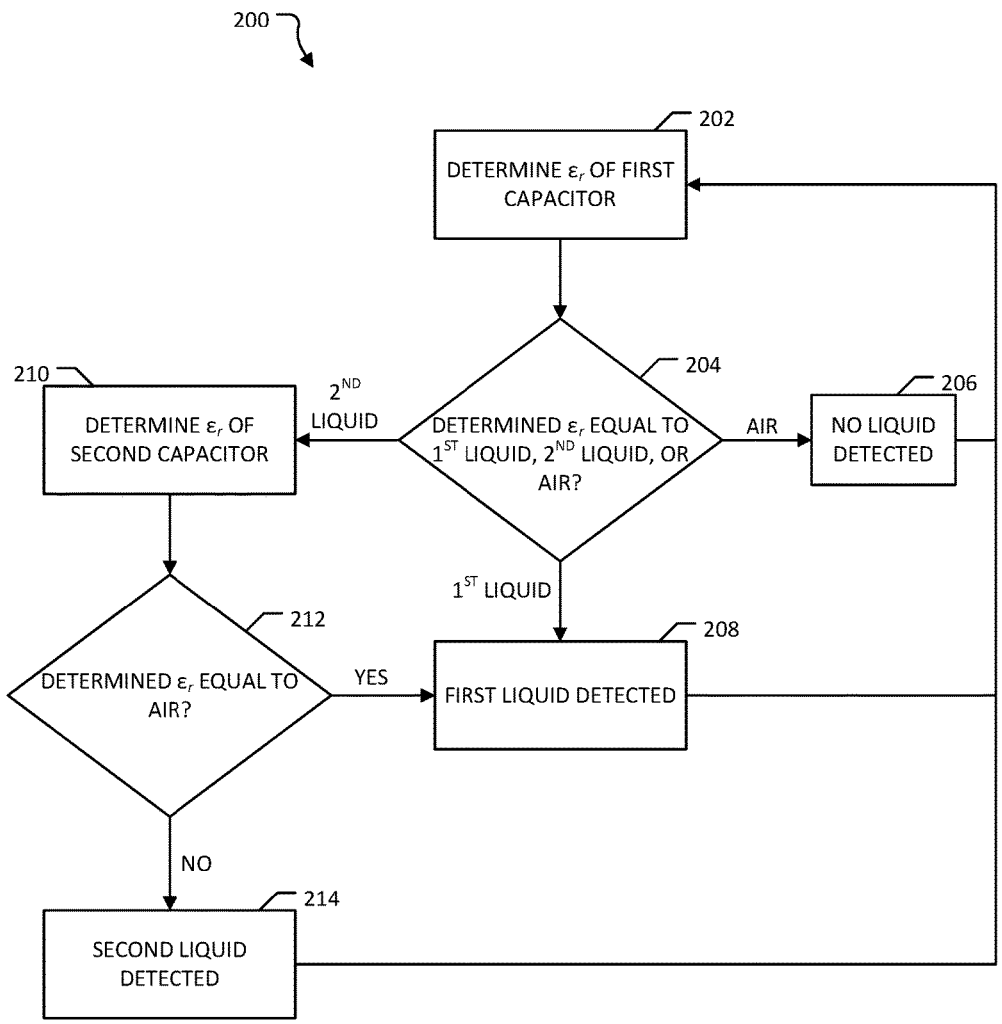
FIG. 4 is a flow chart of a liquid detection verification process according to one embodiment of the present invention.

Referring to FIG. 4, a flow diagram of a method or process 200 for verifying a detection of a liquid in a two liquid system or environment is illustrated. Typically, the multi-capacitor liquid detection device 100 can be implemented to carry out the process 200. In some instances, the process 200 can be implemented to negate false detections of a liquid.

In a typical implementation, the multi-capacitor liquid detection device 100 can be placed in a container, system, or environment that includes, or can be capable of receiving, two immiscible liquids and air. For instance, a container may be a bilge in a boat where water and oil may mix. In one example, the multi-capacitor liquid detection device 100 can be placed in the bilge to determine when oil has entered the bilge with water to send a signal to shut off a bilge pump such that oil is not pumped to an open body of water.

In a first block 202, a relative permittivity ($\varepsilon_r$) of the first capacitor 120 can be determined. Typically, a capacitance of the first capacitor 120 can be measured by the capacitive sensor 108. The microcontroller 106 can then determine the relative permittivity of the first capacitor 120 based on the capacitance measured. As can be appreciated, the power supply 112 can be adapted to provide an electrical charge to the first capacitor 120 and the second capacitor 122.

After determining the relative permittivity of the first capacitor 120 in block 202, the process 200 can move to decision block 204. In decision block 204, the microcontroller 106 can determine whether the relative permittivity indicates a detection of air, a first liquid with a higher permittivity, or a second liquid with a lower permittivity. If the microcontroller 106 determines the relative permittivity indicates air, the process 200 can move to block 206. In block 206, the microcontroller 106 can determine that air has been detected and the process 200 can return to block 202 after determining that no liquid has been detected. In some instances, the multi-capacitor liquid detection device 100 can send a signal to a user that no liquid has been detected in block 206.

If the microcontroller 106 determines that the measured relative permittivity indicates a detection of the first liquid, the process 200 can move to block 208. In block 208, the microcontroller 106 can determine that the first liquid has been detected. The process 200 can then return to block 202. In some instances, the multi-capacitor liquid detection device 100 can send a signal to the user that the first liquid has been detected.

The process 200 can move to block 210 if the microcontroller 106 determines the measured relative permittivity indicates detection of the second liquid. In block 210, the capacitive sensor 108 can measure a capacitance of the second capacitor 122. The microcontroller 106 can then determine a relative permittivity between the second pair of plates 128 of the second capacitor 122.

After determining the relative permittivity of the second capacitor 122, the process 200 can move to decision block 212. In decision block 212, the microcontroller 106 can determine if the relative permittivity of the second capacitor 122 indicates a detection of air or the second liquid. If the relative permittivity of the second capacitor 122 indicates air, the process 200 can move to block 208. In block 208, the microcontroller 106 can determine the first liquid has been detected and the process 200 can move to back to block 202. If the relative permittivity of the second capacitor 122 indicates the second liquid, the process 200 can move to block 214.

In block 214, the microcontroller 106 can determine the second liquid has been detected. Depending on an implementation of the multi-capacitor liquid detection device 100, the process 200 may return to block 202 and be adapted to continuously repeat.

In some instances, the multi-capacitor liquid detection device 100 can send a signal to the user that the second liquid has been detected. Depending on an implementation of the multi-capacitor liquid detection device 100, the multi-capacitor liquid detection device 100 may be adapted to send a signal to another device to indicate the device should shut-off. For instance, if the multi-capacitor liquid detection device 100 is implemented in a bilge, the device 100 may send a signal to a pump in the bilge to turn off if oil is detected.

An Example Multi-Capacitor Liquid Detection Device

Figure 5A:
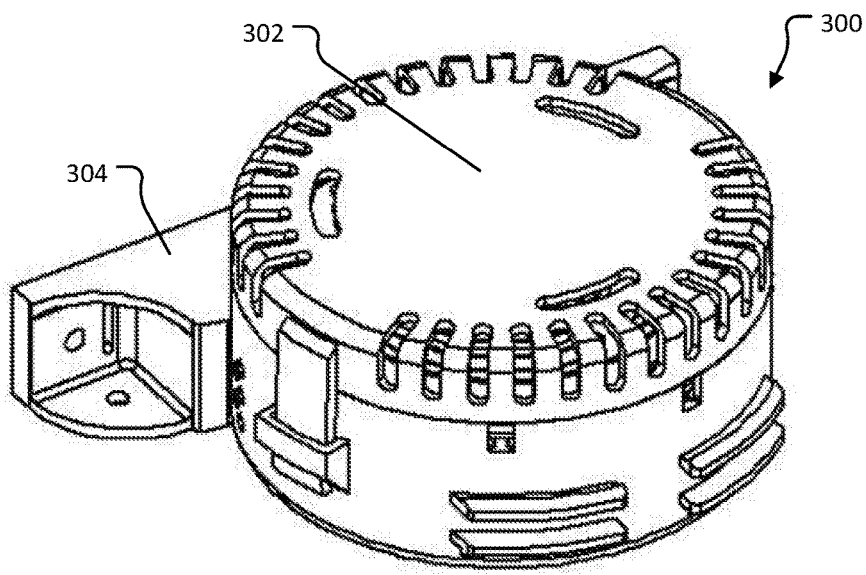
FIG. 5A is a bottom perspective view of a multi-capacitor liquid detection device according to one embodiment of the present invention.
Figure 5B:
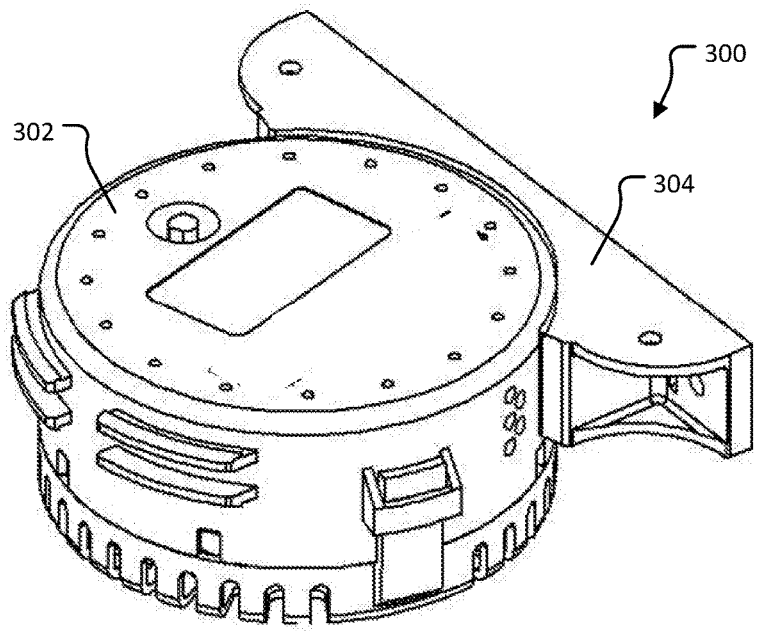
FIG. 5B is a top perspective view of a multi-capacitor liquid detection device according to one embodiment of the present invention.

Referring to FIGS. 5A-5B, a detailed diagram of an example multi-capacitor liquid detection device 300 is illustrated. As shown, the multi-capacitor liquid detection device 300 can include a housing 302 and a mounting bracket 304.

As can be appreciated, the device 300 can include each of the previously mentioned components of the first embodiment multi-capacitor liquid detection device. The device 300 can include a control module and a capacitor assembly located inside the housing 302 of the device 300.

Referring to FIG. 5A, a bottom perspective view of the multi-capacitor liquid detection device 300 is illustrated. As shown, the device 300 can include a plurality of apertures for allowing a liquid to enter the housing 302 of the device 300. As can be appreciated, the capacitor assembly can be located on a bottom side of the device 300 to interface with any liquids that enter the housing 302 via the apertures.

Referring to FIG. 5B, a top perspective view of the multi-capacitor liquid detection device 300 is illustrated. As can be appreciated, the control module can be located on an upper side of the device 300.

Of note, the mounting bracket 304 can be implemented to secure the device 300 at a predetermined height. For instance, the device 300 may need to be placed at a particular height for an application and the mounting bracket 304 can be implemented to secure the device at the particular height.

In one example, the mounting bracket 304 can be removed and the device 300 can be designed to float on a body of water.

Alternative Embodiments and Variations

The various embodiments and variations thereof, illustrated in the accompanying Figures and/or described above, are merely exemplary and are not meant to limit the scope of the invention. It is to be appreciated that numerous other variations of the invention have been contemplated, as would be obvious to one of ordinary skill in the art, given the benefit of this disclosure. All variations of the invention that read upon appended claims are intended and contemplated to be within the scope of the invention.

I claim:

1. A multi-capacitor liquid detection device for use in a two liquid environment, the device comprising:
   a microcontroller;
   a capacitive sensor operatively coupled to the microcontroller;
   a first parallel plate capacitor connected to the capacitive sensor, the first parallel plate capacitor including a first pair of plates having a first height;
   a second parallel plate capacitor connected to the capacitive sensor, the second parallel plate capacitor including a second pair of plates having a second height; and
   a mounting plate, wherein the first pair of plates and the second pair of plates are each coupled to the mounting plate with a bottom of the first pair of plates extending a predetermined distance past a bottom of the second pair of plates.

2. The multi-capacitor liquid detection device of claim 1, wherein the predetermined distance is based on a dielectric constant for (i) air, (ii) a first liquid, and (iii) a second liquid.

3. The multi-capacitor liquid detection device of claim 1, wherein a top side of the first pair of plates and a top side of the second pair of plates are each coupled to the mounting plate.

4. The multi-capacitor liquid detection device of claim 1, wherein the predetermined distance is defined by a difference between the first height and the second height.

5. The multi-capacitor liquid detection device of claim 1, wherein the microcontroller and the capacitive sensor are coupled to a first side of the mounting plate and the first parallel plate capacitor and the second parallel plate capacitor are coupled to a second side of the mounting plate.

6. A method of implementing the multi-capacitor liquid detection device of claim 1, the method comprising:
   placing the multi-capacitor liquid detection device in an environment adapted to receive a first liquid, a second liquid, and air;
   measuring a capacitance of the first parallel plate capacitor and determining a relative permittivity based on the measured capacitance;
   determining if the relative permittivity of the first parallel plate capacitor matches a dielectric constant of the first liquid, the second liquid, or air; and
   verifying the second liquid is present in the environment when the relative permittivity of the first parallel plate capacitor matches the dielectric constant of the second liquid.

7. The method of claim 6, wherein the step of verifying the second liquid has been detected includes:
   measuring a capacitance of the second parallel plate capacitor and determining a relative permittivity based on the measured capacitance of the second parallel plate capacitor when the relative permittivity of the first parallel plate capacitor matches the dielectric constant of the second liquid; and
   determining if the relative permittivity of the second parallel plate capacitor matches a dielectric constant of the second liquid or air.

8. The method of claim 7, further comprising:
   sending a signal indicating the second liquid has been detected when the relative permittivity of the second parallel plate capacitor matches the dielectric constant of the second liquid.

9. The method of claim 7, further comprising:
   sending a signal indicating the first liquid has been detected when the relative permittivity of the second parallel plate capacitor matches the dielectric constant of air.

10. A method for negating a false detection of a liquid in a two liquid system, the method comprising:
    providing a multi-capacitor liquid detection device, the device including a first parallel plate capacitor and a second parallel plate capacitor;
    wherein a bottom of the first parallel plate capacitor is located a predetermined distance below a bottom of the second parallel plate capacitor;
    determining a relative permittivity of the first parallel plate capacitor;
    determining if the relative permittivity of the first parallel plate capacitor matches a dielectric constant of a first liquid, a second liquid, or air; and
    verifying the second liquid has been detected when the relative permittivity of the first parallel plate capacitor matches the dielectric constant of the second liquid.

11. The method of claim 10, wherein the dielectric constant of the first liquid is greater than the dielectric constant of the second liquid.

12. The method of claim 10, wherein the step of verifying the second liquid has been detected includes:

determining a relative permittivity of the second parallel plate capacitor when the relative permittivity of the first parallel plate capacitor matches the dielectric constant of the second liquid; and determining if the relative permittivity of the second parallel plate capacitor matches a dielectric constant of the second liquid or air.

13. The method of claim 12, further comprising:
sending a signal indicating the second liquid has been detected when the relative permittivity of the second parallel plate capacitor matches the dielectric constant of the second liquid.

14. The method of claim 12, further comprising:
sending a signal indicating the first liquid has been detected when the relative permittivity of the second parallel plate capacitor matches the dielectric constant of air.

15. The method of claim 10, wherein the multi-capacitor liquid detection device includes:
a microcontroller;
a capacitive sensor operatively coupled to the microcontroller;
the first parallel plate capacitor connected to the capacitive sensor, the first parallel plate capacitor including a first pair of plates having a first height; and
the second parallel plate capacitor connected to the capacitive sensor, the second parallel plate capacitor including a second pair of plates having a second height.

16. The method of claim 10, wherein the predetermined distance is based on a dielectric constant for (i) air, (ii) the first liquid, and (iii) the second liquid.

17. The method of claim 15, wherein the capacitive sensor is adapted to measure a relative permittivity of the first capacitor and the second capacitor.

18. A method for negating a false detection of a liquid in a two liquid system, the method comprising:
providing a multi-capacitor liquid detection device, the device including:
a microcontroller;
a capacitive sensor operatively coupled to the microcontroller;
a first parallel plate capacitor connected to the capacitive sensor; and
a second parallel plate capacitor connected to the capacitive sensor, wherein a bottom of the first parallel plate capacitor is located a predetermined distance below a bottom of the second parallel plate capacitor;
measuring a capacitance of the first parallel plate capacitor and determining a relative permittivity based on the measured capacitance;
determining if the relative permittivity of the first parallel plate capacitor matches a dielectric constant of a first liquid, a second liquid, or air;
measuring a capacitance of the second parallel plate capacitor and determining a relative permittivity based on the measured capacitance of the second parallel plate capacitor when the relative permittivity of the first parallel plate capacitor matches the dielectric constant of the second liquid; and
determining if the relative permittivity of the second parallel plate capacitor matches a dielectric constant of the second liquid or air;
sending a signal indicating the second liquid has been detected when the relative permittivity of the second parallel plate capacitor matches the dielectric constant of the second liquid.

19. The method of claim 18, the method further comprising:
sending a signal indicating the first liquid has been detected when the relative permittivity of the second parallel plate capacitor matches the dielectric constant of air.

20. The method of claim 18, wherein (i) the two liquid system includes the first liquid, the second liquid, and air; and (ii) the dielectric constant of the first liquid is greater than the dielectric constant of the second liquid.

* * * * *